US009518901B2

(12) United States Patent
Hayashizaki et al.

(10) Patent No.: US 9,518,901 B2
(45) Date of Patent: Dec. 13, 2016

(54) PRETREATMENT METHOD OF BIOLOGICAL SAMPLE, DETECTION METHOD OF RNA, AND PRETREATMENT KIT

(75) Inventors: Yoshihide Hayashizaki, Yokohama (JP); Kengo Usui, Yokohama (JP); Saori Goda, Yokohama (JP); Kazuhito Nomura, Yokohama (JP); Yuki Kawai, Yokohama (JP)

(73) Assignee: KABUSHIKI KAISHA DNAFORM, Kanagawa (JP)

( * ) Notice: Subject to any disclaimer, the term of this patent is extended or adjusted under 35 U.S.C. 154(b) by 0 days.

(21) Appl. No.: 13/807,605

(22) PCT Filed: Jun. 28, 2012

(86) PCT No.: PCT/JP2012/066622
§ 371 (c)(1),
(2), (4) Date: Jul. 26, 2013

(87) PCT Pub. No.: WO2013/002354
PCT Pub. Date: Jan. 3, 2013

(65) Prior Publication Data
US 2013/0302783 A1 Nov. 14, 2013

(30) Foreign Application Priority Data
Jun. 29, 2011 (JP) ................. 2011-145040

(51) Int. Cl.
| C12Q 1/68 | (2006.01) |
| C12P 19/34 | (2006.01) |
| C12P 19/00 | (2006.01) |
| C12P 19/26 | (2006.01) |
| C12P 19/28 | (2006.01) |
| C12P 19/30 | (2006.01) |
| G01N 1/34 | (2006.01) |
| C12N 15/10 | (2006.01) |

(52) U.S. Cl.
CPC ............. *G01N 1/34* (2013.01); *C12N 15/1003* (2013.01); *C12Q 1/6806* (2013.01)

(58) Field of Classification Search
None
See application file for complete search history.

(56) References Cited

U.S. PATENT DOCUMENTS

| 5,455,166 A | 10/1995 | Walker | |
| 5,593,835 A * | 1/1997 | Rando et al. | 435/6.18 |
| 5,679,532 A * | 10/1997 | Repine | 435/7.1 |
| 5,712,124 A | 1/1998 | Walker | |
| 5,743,843 A * | 4/1998 | Berman et al. | 600/9 |
| 6,410,278 B1 | 6/2002 | Notomi et al. | |
| 6,428,990 B1 * | 8/2002 | Mukerji et al. | 435/134 |
| 6,472,187 B1 | 10/2002 | Tonoike et al. | |
| 2002/0168676 A1 | 11/2002 | Notomi et al. | |
| 2004/0132144 A1 | 7/2004 | Notomi et al. | |
| 2005/0123965 A1 | 6/2005 | Yamashita et al. | |
| 2005/0130131 A1 * | 6/2005 | Salahuddin | C07K 14/005 435/5 |
| 2007/0124825 A1 * | 5/2007 | Nicolas et al. | 800/8 |
| 2007/0190531 A1 | 8/2007 | Mitani et al. | |
| 2007/0190561 A1 | 8/2007 | Morin et al. | |
| 2007/0238113 A1 | 10/2007 | Kanda et al. | |
| 2008/0227104 A1 | 9/2008 | Hayashizaki et al. | |
| 2009/0098566 A1 | 4/2009 | Notomi et al. | |
| 2010/0015621 A1 * | 1/2010 | Chang | C12Q 1/6806 435/6.18 |
| 2010/0035331 A1 | 2/2010 | Tsuchiya et al. | |
| 2010/0092971 A1 | 4/2010 | Okamoto et al. | |
| 2011/0117019 A1 * | 5/2011 | Hawkins | 424/9.1 |

FOREIGN PATENT DOCUMENTS

| CN | 1637012 | 7/2005 | |
| CN | 101427783 | 5/2009 | |
| CN | 101449830 | 6/2009 | |
| CN | 101961346 | 2/2011 | |
| DE | EP 1911844 A1 * | 4/2008 | ......... C12N 15/1006 |
| JP | 7-114718 | 12/1995 | |
| JP | 2000-300298 | 10/2000 | |
| JP | 2001-029078 | 2/2001 | |

(Continued)

OTHER PUBLICATIONS

Chomczynski et al. "Single-Step Method of RNA Isolation by Acid Guanidinium Thiocyanate-Phenol-Chloroform Extraction" Analytical Biochemistry, vol. 162, pp. 156-159 (1987).*
Al-Soud et al., "Purification and Characterization of PCR-Inhibitory Components in Blood Cells," Journal of Clinical Microbiology, 2001, vol. 39, No. 2, pp. 485-493.*
Goldenberger et al., "A Simple 'Universal' DNA Procedure Using SDS and Proteinase K Is Compatible with Direct PCR Amplification," PCR Methods and Applications, 1995, vol. 4, pp. 368-370.*
Pastorino et al., "Development of a TaqMan® RT-PCR assay without RNA extraction step for the detection and quantification of African Chikungunya viruses," Journal of Virological Methods, 2005, vol. 124, pp. 65-71.*
González-Chávez, et al., Lactoferrin: structure, function and applications:, International Journal of Antimicrobial Agents, vol. 33, issue 4, pp. 301.e1-301.e8, 2009.
L. Adlerova, et al., "Lactoferrin: a review", Veterinarni Medicina, vol. 53, No. 9, pp. 547-468, 2008.

(Continued)

*Primary Examiner* — Young J Kim
(74) *Attorney, Agent, or Firm* — Hamre, Schumann, Mueller & Larson, P.C.

(57) ABSTRACT

The present invention is to provide a pretreatment method that allows RNA to be detected promptly and simply. RNA degradation activity due to lactoferrin present in the human rhinal mucosa is inhibited, for example, by adding iron ion and carbonate ion to a biological sample that contains the human rhinal mucosa. With the pretreated biological sample, an RNA virus gene can be amplified by a reverse transcriptase. Iron ion and carbonate ion can also inhibit reverse transcriptase inhibition due to lysozyme C contained in the human rhinal mucosa. Further, it is preferable to remove the envelope of the RNA virus by adding SDS to the biological sample that contains the human rhinal mucosa.

9 Claims, 7 Drawing Sheets

(56) References Cited

FOREIGN PATENT DOCUMENTS

| JP | 2005-192409 | 7/2005 |
|---|---|---|
| JP | 2006-087394 | 4/2006 |
| JP | 2007-028985 | 2/2007 |
| JP | 2009-514551 | 4/2009 |
| JP | 4370385 | 9/2009 |
| JP | 2009-247250 | 10/2009 |
| JP | 2010-505396 | 2/2010 |
| JP | 2011-019505 | 2/2011 |
| WO | 00/28082 | 5/2000 |
| WO | 02/078463 | 10/2002 |
| WO | 2005/063977 | 7/2005 |
| WO | 2007/056463 | 5/2007 |
| WO | 2007/094506 | 8/2007 |
| WO | 2007/108712 | 9/2007 |
| WO | 2008/040126 | 4/2008 |

OTHER PUBLICATIONS

Finkbeiner, et al., "Reverse Transcription-Polymerase Chain Reaction (RT-PCR) Phenotypic Analysis of Cell Cultures of Human Tracheal Epithelium, Tracheobronchial Glands, and Lung Carcinomas", American Journal of Respiratory Cell and Molecular Biology, vol. 9, No. 5, pp. 547-556, 1993—Abstract only.

Kanamori-Katayama et al., "Unamplified cap analysis of gene expression on a single-molecule sequencer", Genome Research, 2011, vol. 21, pp. 1150-1159.

Kanyshkova et al., "Lactoferrin and Its Biological Functions", Biochemistry (Moscow), 2001, vol. 66, No. 1, pp. 1-7.

Furmanski et al., "Multiple Molecular Forms of Human Lactoferrin: Identification of a Class of Lactoferrins that Possess Ribonuclease Activity and Lack Iron-binding Capacity", J. Exp. Med., 1989, vol. 170, No. 2, pp. 415-429.

Levay et al., "Lactoferrin: A General Review", Haematologica, 1995, vol. 80, No. 3, pp. 252-267.

Raphael et al., "Pathophysiology of Rhinitis: Lactoferrin and Lysozyme in Nasal Secretions", The Journal of Clinical Investigation, 1989, vol. 84, No. 5, pp. 1528-1535.

Wollants, et al., "Evaluation of a norovirus sampling method using sodium dodecyl sulfate/EDTA-pretreated chromatography paper strips", Journal of Virological Methods, vol. 122, No. 1, Dec. 2004, pp. 45-48.

Office Action issued in corresponding European Patent Application No. 12801801.7, Nov. 17, 2015, 6 pages.

* cited by examiner

PRETREATMENT METHOD OF BIOLOGICAL SAMPLE, DETECTION METHOD OF RNA, AND PRETREATMENT KIT

TECHNICAL FIELD

The present invention relates to a pretreatment method of a biological sample that contains RNA, a detection method of RNA, and a pretreatment kit.

BACKGROUND ART

As a method of detecting a virus in a biological sample such as blood or the like, there is a method of detecting the gene of the virus by amplification. However, since the biological sample often contains a substance inhibiting of gene amplification, the biological sample has been applied with pretreatment to remove or inactivate the inhibition substance prior to the gene amplification. As the pretreatment method, for example, there is a method of performing purification by a solid-phase carrier or an ion-exchange resin after treating the biological sample with a surfactant, a chaotropic agent, or the like or by heating (Patent Documents 1 to 3). However, these methods require special apparatuses and plural operation steps and therefore are complicated.

Especially, in the detection of the virus whose gene is RNA, since amplification is performed after converting an RNA gene to DNA by a reverse transcriptase, a ribonuclease (RNase) and a reverse transcriptase-inactivating substance also need to be removed or inactivated. Therefore, conventional pretreatment methods further require complicated operations. As the pretreatment method of the biological sample that contains RNA virus, for example, addition of polyamine or sulfated polysaccharides has been known (Patent Document 4). However, the addition of polyamine or sulfated polysaccharides has the possibility of complicating the pretreatment and of causing the polyamine and sulfated polysaccharides to be bonded to the RNA gene and the DNA generated by the reverse transcriptase; and therefore the addition of polyamine or sulfated polysaccharides has the possibility of inhibiting the gene amplification.

The influenza virus is a kind of RNA virus, and the determination of whether the influenza virus is novel or seasonal is clinically very important. As the biological sample for detecting the influenza virus, the rhinal mucosa is commonly used. The detection of the influenza virus should be performed at a clinical practice. Therefore, the establishment of a prompt and simple detection method of influenza virus using the human rhinal mucosa is desired. Such a demand is not limited to the influenza virus and the establishment of such a method is also demanded to general RNA virus detection. Further, the establishment of such a method is demanded not only to the detection of the RNA virus but also to the detection of RNA itself other than the gene.

RELATED ART DOCUMENT

Patent Document

[Patent Document 1] JP 2009-247250 A
[Patent Document 2] WO 2007/094506
[Patent Document 3] JP 2006-87394 A
[Patent Document 4] JP 2001-29078 A

DISCLOSURE OF THE INVENTION

Problem to be Solved by the Invention

The present invention is intended to provide a pretreatment method of a biological sample that allows RNA to be detected promptly and simply from a biological sample that contains RNA, a detection method of RNA using the pretreatment method, and a pretreatment kit used for the pretreatment method.

Means for Solving Problem

The pretreatment method of the present invention is a method of pretreating a biological sample that contains RNA, the biological sample containing lactoferrin, the method comprising:
applying inhibition treatment of RNA degradation activity due to lactoferrin to the biological sample.

The detection method of the present invention is a method of detecting RNA in a biological sample, the biological sample containing lactoferrin, the method comprising:
a pretreatment step of pretreating the biological sample; and
an RNA-amplified detection step of detecting RNA in the pretreated biological sample by amplification, wherein
the pretreatment step is performed by the pretreatment method of a biological sample of the present invention.

The pretreatment kit of the present invention is a pretreatment kit of a biological sample that contains RNA, the biological sample containing lactoferrin, the kit comprising:
an inhibitor of RNA degradation activity due to lactoferrin.

Effects of the Invention

The inventors of the present invention discovered that a factor inhibiting a reverse transcription/DNA amplification reaction with RNA contained in a human rhinal mucosa sample being used as a template is RNA degradation activity due to lactoferrin. Then, the inventors of the present invention found out that the RNA degradation can be suppressed by simply applying inhibition treatment of RNA degradation activity due to lactoferrin (for example, addition of inhibitor of RNA degradation activity due to lactoferrin) to the human rhinal mucosa sample. Further, the inventors of the present invention discovered that, as another factor inhibiting reverse transcription/DNA amplification reaction present in a human rhinal mucosa sample, lysozyme C suppresses the reverse transcription reaction from RNA to DNA by a reverse transcriptase. Then, the inventors of the present invention found out that the reverse transcriptase inhibitory activity can be suppressed by adding a suppressant of reverse transcriptase inhibitory activity due to lysozyme C. In addition, the inventors of the present invention discovered that, as a result of treating a human rhinal mucosa sample with suppressant treatment of these reverse transcription/DNA amplification reaction inhibition factors (addition of reagent including suppressor), an RNA gene can be amplified directly without undergoing a special purification step, and thereby achieved the present invention. According to the present invention, RNA can be detected promptly and simply from a biological sample that contains RNA.

DESCRIPTION OF EMBODIMENTS

Figure 1:
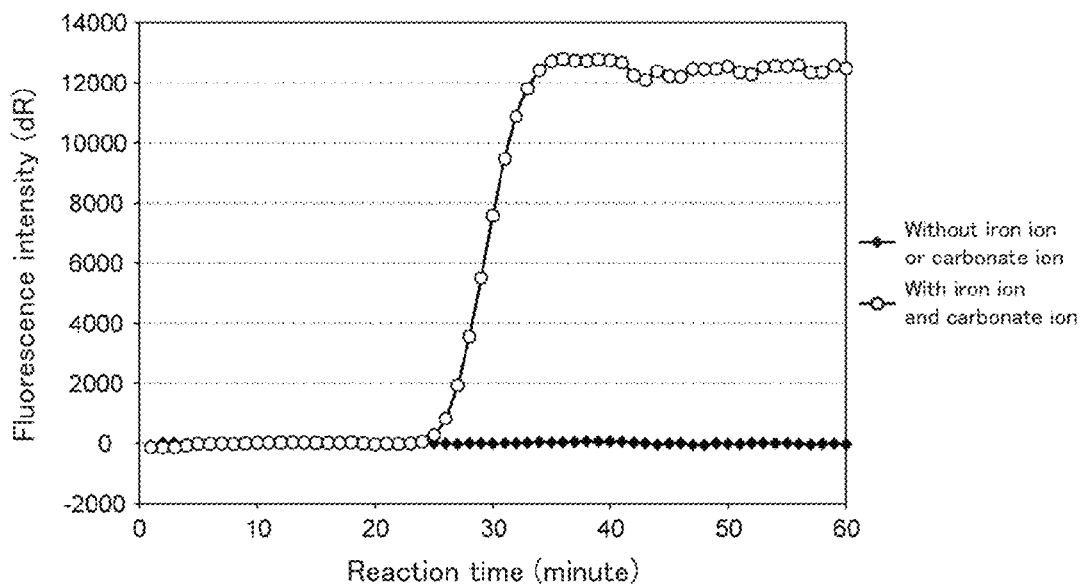
FIG. 1 is a graph showing an example of the detection method of the present invention.

In the pretreatment method of the present invention, preferably, inhibition treatment of RNA degradation activity due to lactoferrin is applied to the biological sample by adding an inhibitor of RNA degradation activity due to lactoferrin to the biological sample.

In the pretreatment method of the present invention, preferably, the biological sample includes rhinal mucosae, sinus mucosae, tracheal mucosae, saliva, secretions from the mouth or the throat, tears, milk, bile, blood (leukocyte), cervical mucosae, internal and external genitalia mucosae, amniotic fluids, or urine of animals.

In the pretreatment method of the present invention, preferably, the animal is human.

In the pretreatment method of the present invention, preferably, the biological sample contains a human rhinal mucosa.

In the pretreatment method of the present invention, preferably, inhibition treatment of reverse transcription inhibitory activity due to lysozyme C is further applied to the biological sample. In this case, preferably, the inhibition treatment of reverse transcription inhibitory activity due to lysozyme C is applied to the biological sample by adding an inhibitor of reverse transcription inhibitory activity due to lysozyme C to the biological sample.

In the pretreatment method of the present invention, preferably, at least one of the RNA degradation activity inhibitor and the reverse transcription inhibitory activity inhibitor contains an iron ion agent and a carbonate ion agent. Note here that, in the present invention, the "iron ion agent" refers to the one that can supply iron ion to the biological sample. Similarly, in the present invention, the "carbonate ion agent" refers to the one that can supply carbonate ion to the biological sample.

In the pretreatment method of the present invention, preferably, the biological sample to which the iron ion agent and the carbonate ion agent are added is subjected to heat treatment. It is because this heat treatment makes it possible to inhibit the RNA degradation activity and the reverse transcription inhibitory activity efficiently.

In the pretreatment method of the present invention, a surfactant may be further added to the biological sample. For example, a polar surfactant is preferably added. For exposing a gene from a virus particle, there is a need to remove the envelope of the virus using a nonionic surfactant. However, there is a possibility that the nonionic surfactant inhibits the functions of the iron ion agent and the carbonate ion agent of the present invention. In this regard, a polar surfactant can remove the envelope of the virus without inhibiting the functions of the iron ion agent and the carbonate ion agent of the present invention. The polar surfactant is preferably SDS. Since there is a possibility that the SDS inhibits DNA polymerase at the time of gene amplification, preferably, SDS is aggregated by adding potassium salt or alumina to the biological sample prior to the gene amplification and SDS is removed by centrifugal separation or filtration.

In the detection method of the present invention, preferably, the amplification of RNA is performed by a gene amplification method using a reverse transcriptase. Preferably, the gene amplification method is an isothermal amplification method using a strand displacement DNA polymerase.

In the detection method of the present invention, for the efflux of an RNA gene from a virus particle using a surfactant, for example, either of the following two steps can be used. Step B is a method of adding a nonpolar surfactant in a gene amplification step and allowing the RNA gene to be eluted from the virus particle by the effects of the nonpolar surfactant and of heating at the time of the gene amplification.

Step A: a step of destroying a virus particle contained in a specimen by a surfactant in the course of pretreatment to allow RNA to be eluted from the virus and, at the same time, suppressing the RNA degradation activity due to lactoferrin and the reverse transcription inhibitory activity due to lysozyme C by inhibition treatment, and subjecting the pretreated liquid to the nucleic acid amplification.

Step B: a step of suppressing the RNA degradation activity due to lactoferrin and the reverse transcription inhibitory activity due to lysozyme C by inhibition treatment without destroying a virus particle in a specimen (i.e., maintaining a virus particle in a specimen), then subjecting the pretreated liquid to a nucleic acid amplification reaction containing a nonpolar surfactant to allow an RNA genome in the virus particle to be eluted by the effects of the surfactant and thermal denaturation, and performing a nucleic acid amplification from the virus genome.

In the Step A, preferably, a polar surfactant is used as the surfactant. The polar surfactant is preferably SDS. In the Step B, preferably, a nonpolar surfactant that does not inhibit a nucleic acid amplification reaction is used as the surfactant.

Preferably, the pretreatment kit of the present invention further includes an inhibitor of reverse transcription inhibitory activity due to lysozyme C.

In the pretreatment kit of the present invention, preferably, at least one of the RNA degradation activity inhibitor and the reverse transcription inhibitory activity inhibitor contains an iron ion agent and a carbonate ion agent. Preferably, the iron ion agent and the carbonate ion agent are contained in a state where the both agents are not in contact with each other.

Next, the present invention will be described in detail.

In the present invention, there is no particular limitation on RNA contained in a biological sample, and the RNA includes all kinds of RNAs obtained from living bodies; host RNAs; and RNAs of bacteria and fungi. The RNA may be RNA of gene or RNA of something else. In the case where the RNA is RNA of gene, the RNA contained in a biological sample is preferably an RNA virus, and particularly preferably an influenza virus.

In the present invention, the biological sample is a sample that contains lactoferrin. The biological sample is preferably a sample that contains human lactoferrin.

Lactoferrin is known to be contained in almost all exocrine secretions of living bodies. Accordingly, examples of the biological sample include secretions from mucosae of upper respiratory tracts such as the nasal cavity, the paranasal sinus, the larynx, the trachea, the bronchus, and the lung; secretions from the mouth and the throat (for example, saliva and the like); secretions from gastrointestinal mucosae; secretions from mucosae of the internal and external genitalia (for example, uterine cervix and the like); secretions from mucosae of the kidney and urinary system; secretions from abdominal mucosae; secretions from thoracic mucosae; secretions from pericardial mucosae; secretions from skins; lacrimal gland secretions; milk; bile; blood (leukocyte); amniotic fluids; urine; and feces of animals. Among them, for example, secretions from mucosae of the nasal cavity and the paranasal sinus; saliva; tears; milk; bile; blood (leukocyte); secretions from the uterine cervix; amniotic fluids; and urine are preferable and they are known to contain lactoferrin in actuality. Among them, the human rhinal mucosa is particularly preferable. Although human is preferable as the animal, animals other than human are applicable. Examples of the animals other than human include cattle, pigs, sheep, horses, camels, and rats.

As described above, lactoferrin is a protein expressed and secreted not only from the rhinal mucosa but also from various tissues. The data obtained by analyzing and comparing the level of the expression amount of RNA encoding a lactoferrin protein in various tissues of human using the data by the CAGE method (Kanamori-Katayama M, et al. Genome Res. (2011) May 19), which is one of the methods of performing an expression analysis using a next-generation sequencer, are shown in Table 1 for reference. The data show that there are various tissues as a tissue of a high expression amount of lactoferrin. This shows a wide range of possibility of the application of the pretreatment method of the present invention.

TABLE 1

| Expression rank | Human tissue sample name | CAGE score (score more than 100) |
|---|---|---|
| 1 | Neutrophil (1) | 22124 |
| 2 | Neutrophil (2) | 13552 |
| 3 | Neutrophil (3) | 11176 |
| 4 | Trachea (1) | 1958 |
| 5 | Eosinophil | 1632 |
| 6 | Myelocyte (1) | 716 |
| 7 | Eye | 548 |
| 8 | Seminal vesicle | 525 |
| 9 | Trachea (2) | 481 |
| 10 | Vas deferens | 480 |
| 11 | Throat | 385 |

TABLE 1-continued

| Expression rank | Human tissue sample name | CAGE score (score more than 100) |
|---|---|---|
| 12 | Salivary gland | 376 |
| 13 | Myelocyte (2) | 350 |
| 14 | Aorta | 273 |
| 15 | Epididymis | 234 |
| 16 | Tonsil | 214 |
| 17 | Submandibular gland | 180 |
| 18 | Myelocyte (3) | 180 |
| 19 | Basophil | 145 |
| 20 | Kidney | 133 |
| 21 | Uterine cervix | 111 |
| 22 | Prostate gland | 108 |

The human rhinal mucosa can be collected from a nasal lavage fluid or by nose-blowing, for example. Preferably, the human rhinal mucosa can be collected by swabbing. The human rhinal mucosa can be used as a biological sample directly or can be used as a biological sample by dispersing or dissolving in a physiological saline, a buffer solution, or the like. As the buffer solution, for preventing degradation in alkalization, the one having a buffering effect on the hydrogen ion concentration from an acidic range to a neutral range can be used. For example, an acetate buffer solution, a phosphate buffer solution, a tartaric acid buffer solution, a borate buffer solution, a citrate buffer solution, a Tris buffer solution, a phosphate buffered saline (PBS), and various Good buffer solutions (MES, Bis-Tris, ADA, PIPES, ACES, MOPSO, BES, MOPS, TES, HEPES, DIPSO, TAPSO, POPSO, HEPPSO, EPPS, Tricine, Bicine, and TAPS) can be used. The pH of the buffer solution is, for example, in the range from 4.0 to 8.0, preferably in the range from 5.0 to 7.0, and more preferably in the range from 5.5 to 6.0. To use MES ($pK_a$=6.15) is most preferable.

As described above, the point of the present invention is the discovery of the following facts: a factor inhibiting a reverse transcription/DNA amplification reaction with RNA in a biological sample being used as a template is RNA degradation activity due to lactoferrin; and the gene amplification of an RNA virus can be performed without applying special purification treatment if the RNA degradation activity due to lactoferrin is inhibited. The inhibition treatment of the RNA degradation activity due to lactoferrin includes, for example, addition of an inhibitor of RNA degradation activity due to lactoferrin to a biological sample and heat treatment of the biological sample. The inhibition treatment may be performed by both the addition of the RNA degradation activity inhibitor and the heat treatment, for example. The temperature of the heat treatment is, for example, in the range from 25 to 100° C., preferably from 30 to 75° C., and more preferably from 37 to 65° C. The time of the heat treatment is, for example, in the range from 1 to 60 minutes, preferably in the range from 2 to 45 minutes, and more preferably in the range from 5 to 30 minutes.

The RNA degradation activity due to lactoferrin can be reduced also by excessively adding RNA (decoy RNA) other than the target RNA.

Various inhibitors can be used for inhibiting the RNA degradation activity due to lactoferrin. As the inhibitor, a bovine placenta-derived RNase inhibitor commonly used in the molecular biology can be used. Further, a specific IgG antibody and an Affibody protein molecule that specifically bind to lactoferrin and inhibit the RNA degradation activity or an RNA/DNA aptamer that can perform screening as a nucleic acid-derived specific binding molecule can be used. Furthermore, low molecular organic compounds such as sulfate, sulfothioate, phosphate, sulfamate, and sulfochloride found by an in sillico binding molecule-searching to lactoferrin can be used.

As the inhibitor of the RNA degradation activity due to lactoferrin, preferably, metal ions belonging to the transition metal and the typical metal can be used. Examples of the metal ion belonging to the transition metal include copper ($Cu^{2+}$, $Cu^{3+}$), nickel ($Ni^{2+}$), iron ($Fe^{2+}$, $Fe^{3+}$), and gold ($Au^{+}$, $Au^{3+}$); and scandium ($Sc^{3+}$), yttrium ($Y^{3+}$), gadolinium ($Gd^{3+}$), cerium ($Ce^{3+}$), and neodymium ($Nd^{3+}$), which are classified into the light rare earth. As the metal ion belonging to the typical metal, zinc ($Zn^{2+}$) can be used. Note here that these metals can be used alone or used in combination as a mixed reagent.

As the inhibitor of the RNA degradation activity due to lactoferrin, more preferably, an iron ion agent and a carbonate ion agent are used simultaneously. This is because of the following facts: lactoferrin causes high RNA degradation activity when it becomes an apo-form (apo-lactoferrin) that does not contain iron; and the crystal structure of lactoferrin contains iron ion and carbonate ion at a metal-binding domain. It is considered that, by simultaneously providing iron ion and carbonate ion to apo-lactoferrin that does not contain metal ion, lactoferrin can be shifted from an apo-form to a holo-form (holo-lactoferrin) efficiently, and the RNA degradation activity can be suppressed. Although the iron ion agent alone has the inhibitory activity on RNA degradation activity due to lactoferrin, if the iron ion agent is used alone, there is a possibility that the iron ion agent itself expresses the RNA degradation activity when the concentration of the iron ion agent is increased. Since the carbonate ion agent can form insoluble iron carbonate ($Fe_2(CO_3)_3$) by reacting with a surplus iron ion agent, the carbonate ion agent is effective as means for suppressing the degradation of RNA due to the surplus iron ion itself. Therefore, by adding the carbonate ion agent together with the iron ion agent, the RNA degradation activity due to lactoferrin can be inhibited and also the RNA degradation activity due to the iron ion agent itself can be inhibited.

As the iron ion agent, the one that can supply trivalent ferric iron ($Fe^{3+}$) is preferable. For example, ferric chloride ($FeCl_3$), ferric nitrate ($Fe(NO_3)_3$), and ferric sulfate ($Fe_2(SO_4)_3$) are preferable and the aqueous solutions thereof are more preferable. Here, from the viewpoint of the stability in the aqueous solution, ferric sulfate is preferably used.

As the carbonate ion agent, the one that can supply carbonate ion ($CO_3^{2-}$) is preferable. For example, sodium hydrogen carbonate can be used, and the aqueous solution of sodium hydrogen carbonate is preferable.

In the solution (biological sample) in which $Fe^{3+}$ and $CO_3^{2-}$ are present at the same time, for example, the concentration of $Fe^{3+}$ is in the range from 2 to 6 mM and the concentration of $CO_3^{2-}$ is in the range from 5 to 20 mM. With respect to the concentrations of the iron ion agent and the carbonate ion agent, for example, the concentration of $Fe_2(SO_4)_3$ is in the range from 1 to 3 mM and the concentration of $NaHCO_3$ is in the range from 5 to 20 mM. More preferably, the concentration of $Fe_2(SO_4)_3$ is about 2.5 mM and the concentration of $NaHCO_3$ is about 10 mM.

As described above, in the case where SDS, which is the polar surfactant, is added to the biological sample, since there is a possibility that SDS inhibits DNA polymerase at the time of gene amplification, as described above, it is preferable to remove SDS from the biological sample using alumina and the like. Note here that, in the case of using the alumina, since the adsorption of polar molecules other than SDS to the alumina may occur, for example, there is a possibility that RNA, DNA, and the like contained in the biological sample are also absorbed to the alumina and removed from the biological sample. Here, SDS and iron ion form a precipitate by interaction. SDS can be removed from the biological sample also by utilizing this precipitate-forming ability. From this viewpoint, it is preferable to set the concentration of the iron ion contained in the biological sample high. The concentration of the iron ion (for example, $Fe^{3+}$) is preferably 1 mM or more, more preferably 2 mM or more, and yet more preferably 2.5 mM or more. There is no particular limitation on the upper limit of the concentration of the iron ion, and the upper limit is, for example, 10 mM or less or 5 mM or less. For example, the precipitate of SDS and iron ion preferably is removed from the biological sample by centrifugal separation or filtration. In the case of removing the precipitate by the filtration, preferably, a size exclusion filter (ultrafiltration filter) is used for the filtration. For example, the pore size of the ultrafiltration filter can be in the range from 0.1 to 0.45 μm, and is preferably 0.22 μm. As the ultrafiltration filter, for example, "Millex HV" (product name; membrane pore size: 0.22 μm) produced by Millipore Corporation can be used.

Lysozyme C contained in a rhinal mucosa sample in high proportion inhibits reverse transcriptase activity that synthesizes DNA with RNA being used as a template. As described above, in the present invention, preferably, inhibition treatment of reverse transcription inhibitory activity due to lysozyme C is applied to a biological sample such as a rhinal mucosa sample. The inhibition treatment of reverse transcription inhibitory activity due to lysozyme C includes, for example, addition of an inhibitor of reverse transcription inhibitory activity due to lysozyme C and heat treatment of the biological sample. The inhibition treatment may be performed by both the addition of the reverse transcription inhibitory activity inhibitor and the heat treatment, for example. As the inhibitor of reverse transcription inhibitory activity due to lysozyme C, for example, a specific IgG antibody and an Affibody protein molecule that specifically bind to lysozyme C and suppress the reverse transcription inhibitory activity or an RNA/DNA aptamer that can perform screening as a nucleic acid-derived specific binding molecule can be used. More preferably, the reverse transcription inhibitory activity can be suppressed by addition of an iron ion agent (for example, the one that can supply trivalent iron ion) and a carbonate ion agent. The temperature of the heat treatment is, for example, in the range from 25 to 100° C., preferably in the range from 30 to 75° C., and more preferably in the range from 37 to 65° C. The time of the heat treatment is, for example, in the range from 1 to 60 minutes, preferably in the range from 2 to 45 minutes, and more preferably in the range from 5 to 30 minutes.

Preferably, the biological sample to which the iron ion agent and the carbonate ion agent are added is applied with heat treatment. It is considered that the heat treatment has the effect of causing the structural fluctuation of lactoferrin, and this makes it possible to increase the effects of the iron ion agent and the carbonate ion agent on lactoferrin and to suppress the RNA degradation activity more effectively. The conditions of the heat treatment are as follows: for example, the temperature is in the range from 37 to 60° C. and the time is in the range from 5 to 30 minutes. For example, in the case where the temperature is 37° C., the heat treatment is performed for 30 minutes, and in the case where the temperature is 60° C., the heat treatment is performed for 5 minutes.

As a step without applying the aforementioned heat treatment, a very small quantity of protein denaturing agent can be used. Specifically, guanidinium hydrochloride, guanidine thiocyanate, and urea can be used (the surfactants will be described below).

Preferably, a polar surfactant is added to the biological sample to which the iron ion agent and the carbonate ion agent are added for removing the envelope of a virus particle. As the polar surfactant, an anionic surfactant is preferable. Specifically saponin, sodium octanoate, sodium decanoate, sodium laurate, sodium myristate, sodium palmitate, sodium stearate, perfluorooctanoate (PFOA), perfluorononanoic acid, sodium n-lauroyl sarcosinate, sodium cocoyl glutamate, α-sulfonated fatty acid methyl esters, 1-hexanesulfonic acid sodium salt, 1-octanesulfonic acid sodium salt, 1-decanesulfonic acid sodium salt, 1-dodecanesulfonic acid sodium salt, perfluorobutanesulfonic acid, sodium linear alkylbenzene sulfonate, sodium naphthalenesulfonate, naphthalenedisulfonic acid disodium salt, naphthalenetrisulfonic acid trisodium salt, sodium butylnaphthalenesulfonate, perfluorooctanesulfonate (PFOS), sodium lauryl sulfate, sodium myristyl sulfate, sodium polyoxyethylene alkylphenol sulfonate, ammonium lauryl sulfate, lauryl phosphate, sodium lauryl phosphate, potassium lauryl phosphate, sodium N-laurylsarcosinate, sodium n-tetradecyl sulphate (STS), sodium n-dodecyl sulphate, sodium cholate, sodium glycocholate, sodium deoxycholate (DOC), sodium glycodeoxycholate, sodium chenodeoxycholate, sodium taurocholate, sodium taurochenodeoxycholate, sodium taurodehydrocholate, sodium taurodeoxycholate, sodium taurolithocholate, and sodium tauroursodeoxycholate can be used. More preferably, sodium n-dodecyl sulfate (SDS) is added. The concentration of the surfactant to be added is, for example, 0.1 w/v % or less in the case of SDS. In the case where SDS is added, the RNA degradation activity due to lactoferrin can be inhibited by the iron ion agent and the carbonate ion agent promptly without applying the heat treatment. The pretreatment of a human rhinal mucosa sample with the addition of the polar surfactant is defined as a pretreatment method according to the following Step A.

Step A: a step of destroying a virus particle contained in a specimen by a polar surfactant in the course of pretreatment to allow RNA to be eluted from the virus and, at the same time, suppressing the RNA degradation activity due to lactoferrin and the reverse transcription inhibitory activity due to lysozyme C by inhibitors, and subjecting the pretreated liquid to the nucleic acid amplification.

The addition of the polar surfactant is optional, and the RNA gene of the RNA virus can be amplified by the pretreatment of the present invention without adding the polar surfactant. In this case, the premise is that the release of the RNA genome from the virus occurs in the course of the nucleic acid amplification reaction. In the case where the reverse transcription reaction is performed at, for example, 50 to 60° C. in the nucleic acid amplification from RNA, the thermal denaturation effect on the virus envelope can be expected, and the RNA genome can be released from the RNA virus. More preferably, a nonionic surfactant that has the effect of destroying the virus envelope and that does not inhibit the nucleic acid amplification reaction can be added to the nucleic acid amplification reaction solution. Specifically, as the nonionic surfactant, Tween (registered trademark) series surfactants (Tween 20, Tween 40, Tween 60, and Tween 80), Brij (registered trademark) series surfactants (Brij-76, Brij-96, Brij-56, Brij-58, and Brij-35), Span series surfactants (Span-20, Span-40, and Span-60), POE (9 and 10) nonylphenyl ether (Triton (registered trademark) N-101), Triton (registered trademark) X-100, Triton X-114, digitonin, APO-10, APO-12, BIG CHAP, cyclohexyl-n-ethyl-β-D-maltoside, n-decanoylsucrose, n-dodecanoylsucrose, n-decyl-β-D-maltopyranosid, n-decyl-β-D-thiomaltoside, n-dodecyl-β-D-glucopyranoside, n-dodecyl-β-D-maltoside, ELUGENT (registered trademark), GENAPOL (registered trademark) C-100, GENAPOL X-80, GENAPOL X-100, HECAMEG, n-heptyl-β-D-glucopyranoside, n-heptyl-β-D-thioglucopyranoside, n-hexyl-β-D-glucopyranoside, MEGA-8, MEGA-9, MEGA-10, n-nonyl-β-D-glucopyranoside, NP-40, n-octanoyl-β-glucosylamine (NOGA), n-octanoylsucrose, n-octyl-β-D-glucopyranoside, n-octyl-β-D-maltopyranoside, n-octyl-β-D-thioglucopyranoside, n-undecyl-β-D-maltoside, PLUPONIC (registered trademark) F-127, nonoxynol, nonoxynol-9, glyceryl laurate, glyceryl monostearate, sorbitan fatty acid ester, lauric acid diethanolamide, oleic acid diethanolamide, stearic acid diethanolamide, cetanol, stearyl alcohol, and oleyl alcohol can be used.

As described above, in the case where SDS, which is the polar surfactant, is added to the biological sample, there is a possibility that SDS inhibits the DNA polymerase at the time of the gene amplification. Therefore, SDS is removed from the biological sample by the aforementioned methods of using alumina, of forming a precipitate of SDS with iron ion by increasing the concentration of iron ion, and the like. However, there is a case in which SDS remains in the biological sample even after the SDS removal treatment. In the present invention, at the time of the gene amplification of the biological sample that contains SDS, it is preferable to add the nonionic surfactant that does not inhibit the nucleic acid amplification reaction. Thereby, SDS contained in the biological sample is incorporated into the micelle of the nonionic surfactant and the DNA polymerase inhibition due to SDS at the time of the gene amplification is suppressed. Note here that the aforementioned mechanism is merely assumed and the present invention is not limited at all by this description. In the present invention, for the aforementioned purpose, for example, the nonionic surfactant may be added to the biological sample of after the SDS removal treatment at the time of the gene amplification or the nonionic surfactant may be added to the biological sample not subjected to the SDS removal treatment at the time of the gene amplification. Further, for example, the nonionic surfactant may be preliminarily added to the reaction solution of the nucleic acid amplification (gene amplification). As the nonionic surfactant, Triton (registered trademark) X-100 is preferable. The amount of Triton (registered trademark) X-100 to be added can be set suitably according to the concentration of SDS contained in the biological sample, for example. In the case where SDS is contained in the biological sample at 0.1%, Triton (registered trademark) X-100 is preferably contained in the biological sample in the range from 0.1 to 1%, and for example, the concentration of Triton (registered trademark) X-100 may be 0.5%.

As described above, SDS can be removed by adding neutral potassium salt or alumina. As the neutral potassium salt, potassium acetate, citric acid potassium, hydrochloric acid potassium, potassium sulfate, and potassium nitrate can be used. The one having a water solubility is preferable and potassium acetate is more preferable. As the alumina, for example, an alumina particle (average particle size is 1000 nm or less; preferably, average particle size is 200 nm or less; more preferably, average particle size is from 20 to 100 nm) can be used. Also, activated alumina (produced by Wako Pure Chemical Industries, Ltd., molecular weight: 101.96) and the like can be used.

There is no particular limitation on the gene amplification method and examples of the gene amplification method include the PCR method and the isothermal amplification method using a strand displacement DNA polymerase, and the isothermal amplification method is preferable. Examples of the isothermal amplification method include the SDA method (JP H7 (1995)-114718 A) and the amplification method using the turn-back primer (TP) described below, and the isothermal amplification method using TP is preferable.

(Turn-Back Primer)

The turn-back primer contains, at the 3' end, a sequence (Ac') that hybridizes to the 3' end of a target nucleic acid sequence and contains, at the 5' side of the sequence (Ac'), a sequence (B') that hybridizes to a complementary sequence (Bc) of a sequence (B) present at the 5' side relative to the sequence (A).

In the isothermal amplification method using TP, both of a symmetrical form (TP-TP), in which TP is used as both of the forward primer and reverse primer, and an asymmetrical form (TP-XP), in which TP is used as one of the forward primer and the reverse primer and a primer (XP) other than TP is used as the other of the forward primer and the reverse primer, can be employed.

A specific example of the symmetrical form (TP-TP) includes the LAMP method (WO2000/028082). The LAMP method is a method of using a pair of outer primers (OP-OP) in addition to a pair of TPs (TP-TP). OP is a primer that has a function of annealing to the 5' side relative to TP in a template sequence and separating the TP elongated strand by the strand displacement reaction.

Figure 7A:
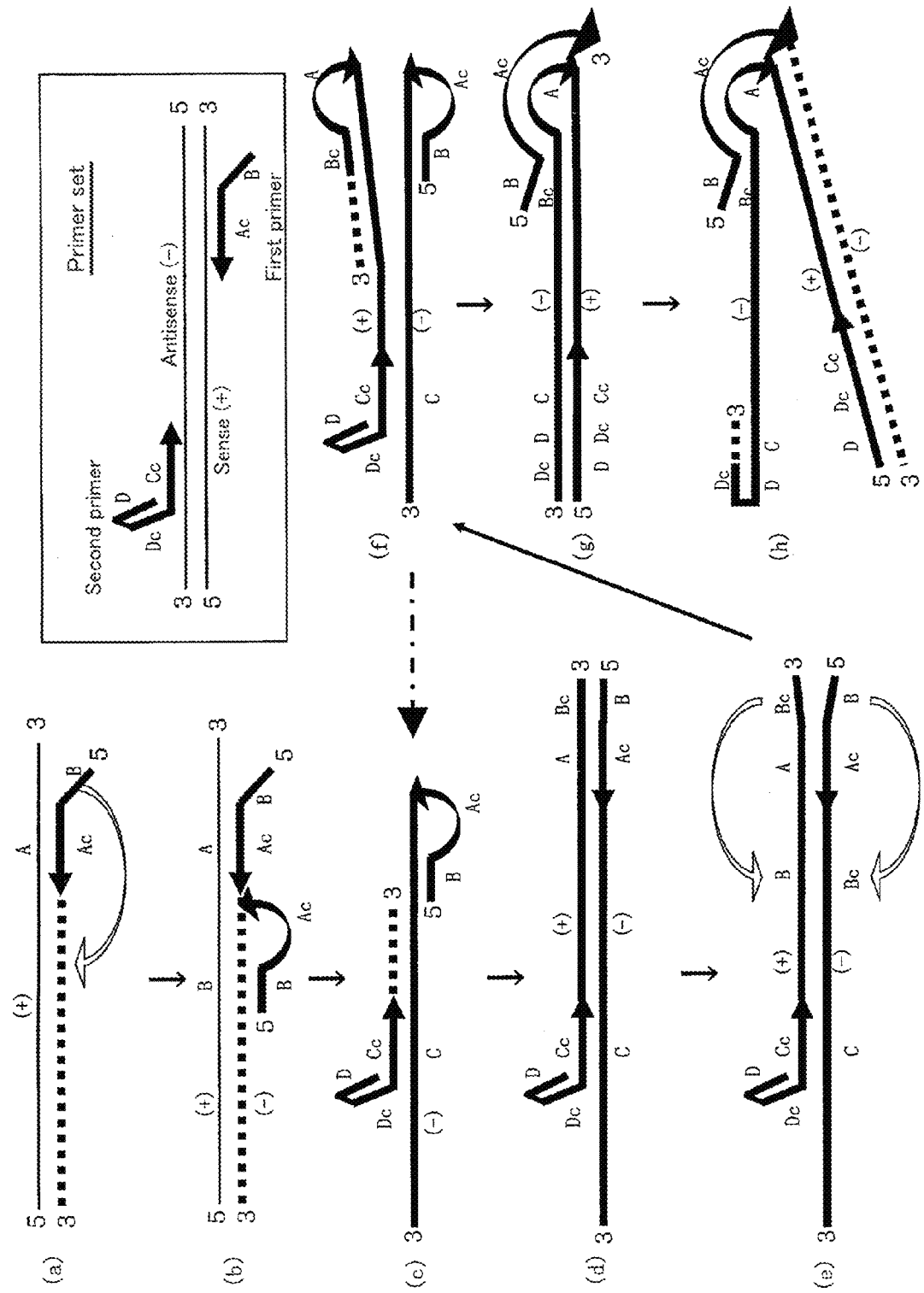
FIG. 7A is a view showing an example of the mechanism of the nucleic acid amplification reaction by a turn-back primer and a folding primer.
Figure 7B:
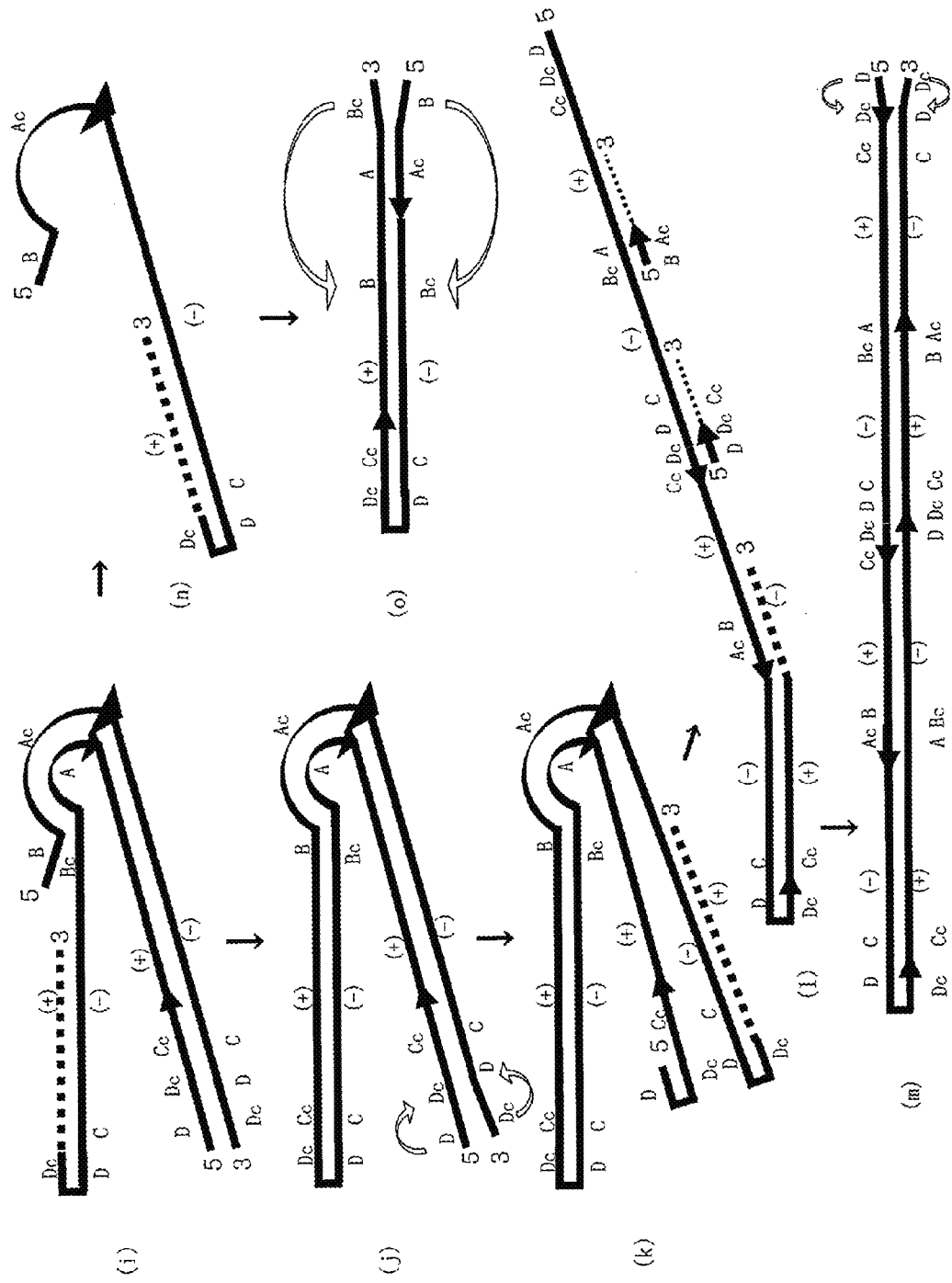
FIG. 7B is a view showing an example of the mechanism of the nucleic acid amplification reaction by a turn-back primer and a folding primer.

Examples of the primer other than TP in the case of the asymmetrical form include a common primer used in the PCR method and the folding primer (FP) described below. In the asymmetrical form, the combination of TP and FP is preferable. An example of the combination form of TP and FP includes the SmartAmp method (registered trademark) (WO2005/063977). FIGS. 7A and 7B show an example of the combination of TP and FP. In addition to the combination of TP and FP, OP can be further used. OP may be used on at least one of a forward primer side and a reverse primer side.

(Folding Primer)

The folding primer contains, at the 3' end, a sequence (Cc') that hybridizes to a sequence (C) at the 3' end of a complementary sequence of a target nucleic acid sequence and contains, at the 5' side of the sequence (Cc'), a folded sequence (D-Dc') that contains two nucleic acid sequences that hybridize to each other at the same strand.

The mechanism of the isothermal amplification using TP-FP is, for example, as follows. The possible mechanism of action of TP and FP to the nucleic acid amplification reaction will be described with reference to FIG. 7 (FIGS. 7A and 7B). In FIG. 7, two sequences that hybridize to each other are shown as the sequences complementary to each other for simplifying the explanation. However, the present invention is not limited thereby. First, TP hybridizes to the sense strand of a target nucleic acid, and the elongation reaction of the primer occurs (FIG. 7(a)). Next, a stem-loop structure is formed on the elongated strand (−), new TP hybridizes to the sequence (A) on the target nucleic acid sense strand that became a single strand by the formation of the stem-loop structure (FIG. 7(b)), the elongation reaction of the primer occurs, and the previously synthesized elongated strand (−) is detached. Next, FP hybridizes to the sequence (C) on the detached elongated strand (−) (FIG. 7(c)), the elongation reaction of the primer occurs, and the elongated strand (+) is synthesized (FIG. 7(d)). At the 3' end of the generated elongated strand (+) and the 5' end of the elongated strand (−), stem-loop structures are formed (FIG. 7(e)), and at the same time as the elongation reaction occurs from the loop tip of the elongated strand (+), which is the free 3' end, the elongated strand (−) is detached (FIG. 7(f)). By the elongation reaction of the loop tip, a hairpin double-stranded nucleic acid in which the elongated strand (−) binds to the 3' side of the elongated strand (+) through the sequence (A) and the sequence (Bc) is generated, TP hybridizes to the sequence (A) and the sequence (Bc) (FIG. 7(g)), and the elongated strand (−) is generated by the elongation reaction (FIGS. 7(h) and 7(i)). Further, the free 3' end is provided by the folded sequence present at the 3' end of the hairpin double-stranded nucleic acid (FIG. 7(h)), by the elongation reaction therefrom (FIG. 7(i)), a single-stranded nucleic acid that has the folded sequences at the both ends and contains the elongated strands (+) and the elongated strands (−) alternately through the sequences derived from TP and FP is generated (FIG. 7(j)). In this single-stranded nucleic acid, since the free 3' end (origin of complementary strand synthesis) is provided by the folded sequence present at the 3' end thereof (FIG. 7(k)), a similar elongation reaction is repeated, and the strand length is doubled per elongation reaction (FIGS. 7(l) and (m)). Further, in the elongated strand (−) from TP detached in FIG. 7(i), since the free 3' end (origin of complementary strand synthesis) is provided by the folded sequence present at the 3' end thereof (FIG. 7(n)), by the elongation reaction therefrom, stem-loop structures are formed at the both ends, and a single-stranded nucleic acid that contains the elongated strands (+) and the elongated strands (−) alternately through the sequences derived from the primers is generated (FIG. 7(o)). Also in this single-stranded nucleic acid, the origin of complementary strand synthesis is provided successively by the formation of the loop at the 3' end, and thereby the elongation reaction therefrom occurs one after another. In the single-stranded nucleic acid automatically extended in this manner, the sequences derived from TP and FP are contained between the elongated strands (+) and the elongated strands (−). Therefore, each primer can hybridize to cause the elongation reaction, and thereby the sense strand and the antisense strand of the target nucleic acid are amplified prominently.

In the case of amplifying an RNA gene, cDNA is generated using a reverse transcriptase and this cDNA is amplified. The SmartAmp method amplifying RNA using a reverse transcriptase in this manner is called the RT-SmartAmp.

There is no particular limitation on the composition of the pretreatment kit of the present invention. For example, the following composition can be employed: 20 mM MES buffer (pH 5.8), 2.5 mM iron sulfate, 20 mM sodium hydrogen carbonate, 0.1% SDS, and 20 mg/ml alumina ($Al_2O_3$).

In the case where iron sulfate and sodium hydrogen carbonate are stored as a mixed solution, a precipitate is formed promptly. Therefore, in the pretreatment kit of the present invention, preferably, two solutions, namely, A solution and B solution are prepared so that iron sulfate and sodium hydrogen carbonate can be provided separately. In this case, for example, the composition of the A solution is as follows: 20 mM MES buffer (pH 5.8), 40 mM sodium hydrogen carbonate, and 0.2% SDS, and the composition of the B solution is as follows: 5 mM iron sulfate and 40 mg/ml alumina. In this case, the B solution that contains iron sulfate is preferably stored in a light-resistant container. Preferably, the A solution and the B solution are prepared as a mixed solution at the ratio of 1:1 at the time of suspending the human rhinal mucosa in a buffer solution.

EXAMPLES

Next, Examples of the present invention will be described. The present invention is not restricted or limited by the Examples.

Example 1

Nucleic Acid Amplification of Template RNA Mixed in Human Rhinal Mucosa

In Example 1, it was examined whether or not the inhibitory activity of the nucleic acid amplification from template RNA contained in a human rhinal mucosa can be suppressed by the pretreatment kit of the present invention. As the pretreatment kit, prepared was a kit (pretreatment reagent) having the following composition: 10 mM MES buffer (pH 5.8), 2.5 mM iron sulfate, 20 mM sodium hydrogen carbonate, 0.1% SDS, and 20 mg/ml activated alumina (produced by Wako Pure Chemical Industries, Ltd., molecular weight: 101.96). The human rhinal mucosa of a healthy subject was suspended in this kit and then $10^7$ copies of the template RNA having the same partial sequence as the virus (influenza A(H1N1)) prepared as below was mixed thereto, and the resultant was used as the sample of Example 1. This sample was subjected to the RT-SmartAmp method and the presence of RNA was detected. As Comparative Example, the nucleic acid amplification was performed in the same manner as described above with the kit prepared in the same manner as described above except that iron sulfate and sodium hydrogen carbonate were not added. The results thereof are shown in FIG. 1. As shown in FIG. 1, in the case where the kit of the present invention was used, the nucleic acid amplification with RNA being used as a template was achieved. In contrast, in Comparative Example, the nucleic acid amplification could not be performed. The RT-Smart-Amp was performed as follows.

In the RT-SmartAmp method in Example 1, the sequence of influenza A (H1N1), the HA region 595-1048 bases, was used as a template RNA to be amplified. For preparing the template RNA, first, PCR was performed using cDNA having the sequence complementary to the HA region, the following primer 1 (SEQ ID NO: 1) and primer 2 (SEQ ID NO: 2), and SYBR Premix Ex Taq (produced by TAKARA BIO INC.).

```
Primer 1
                                     (SEQ ID NO: 1)
5'-CTAATACGACTCACTATAGGGCCATCTACTAGTGCTGACCA-3'

Primer 2
                                     (SEQ ID NO: 2)
5'-CCCTTCAATGAAACCGGCAA-3'
```

Conditions for the PCR were as follows. That is, one cycle of treatment at 95° C. for 30 seconds, 60° C. for 30 seconds, and 72° C. for 30 seconds was repeated for 35 cycles, and then incubation at 72° C. for 3 minutes was performed. With the DNA fragment amplified by this PCR, a template RNA was synthesized using the CUGA7 in-vitro Transcription Kit (produced by NIPPON GENE CO., LTD.).

In the RT-SmartAmp method, in a liquid of 25 μL, the primers (SEQ ID NOs: 3 to 7, produced by Kabushiki Kaisha DNAFORM) and exciton primer (SEQ ID NO: 8, produced by Kabushiki Kaisha DNAFORM, see Japanese Patent No. 4370385) having the following sequences and concentrations were added to a solution that contains 1.4 mM dNTP, 5% DMSO, 20 mM Tris-HCl (pH 8.0), 30 mM potassium acetate, 10 mM sodium sulfate, 8 mM magnesium sulfate, 0.1% Tween 20, 12 unit Aac DNA polymerase, and 0.125 unit AMV Reverse Transcriptase (these concentrations are the final concentrations), and the resultant was used as a reaction solution.

```
FP primer
        (SEQ ID NO: 3, final concentration: 1.82 μM)
5'-GCATTCGCGAAATGATAATACCAGATCC-3'

TP primer
        (SEQ ID NO: 4, final concentration: 1.82 μM)
5'-TTCCATTGCGAATGCACATTCGAAGCAAC-3'

OP primer 1
        (SEQ ID NO: 5, final concentration: 0.23 μM)
5'-ACACTAGTAGAGCCGGGAGA-3'

OP primer 2
        (SEQ ID NO: 6, final concentration: 0.23 μM)
5'-CTGGTGTTTATAGCACCCTT-3'

BP primer
        (SEQ ID NO: 7, final concentration: 0.68 μM)
5'-ACCACTAGATTTCCAG-3'

BP exciton primer
        (SEQ ID NO: 8, final concentration: 0.23 μM)
5'-ACCACZAGATTTCCAG-3'
(Z indicates thymine residue labeled with exciton)
```

Further, the sample prepared by suspending the synthesized template RNA and the human rhinal mucosa in the pretreatment kit was added, the reaction capacity was adjusted to 25 μL, and then the reaction under a constant temperature was performed using the real-time PCR apparatus MX3000p (produced by Agilent Technologies, Inc.) at 60° C. for 90 minutes, and nucleic acid amplification activity was checked by obtaining a fluorescence amplification curve via an FAM filter. As a result, as shown in FIG. 1, nucleic acid amplification from the added template RNA was achieved only with respect to the sample treated with the pretreatment reagent of the present invention.

Reference Example 1

Presence of Lactoferrin and Lysozyme C in Human Rhinal Mucosa

Figure 2:
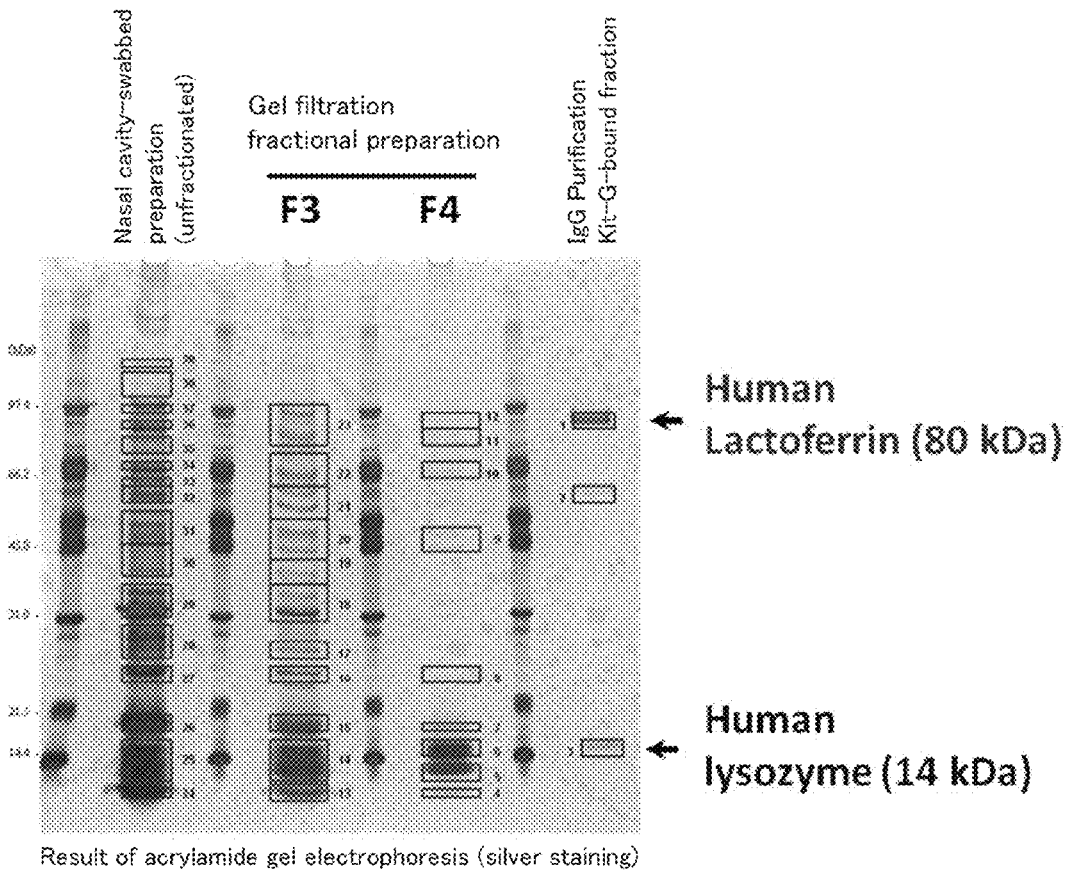
FIG. 2 is an electrophoresis photograph showing the presence of lactoferrin and lysozyme C in a human rhinal mucosa.

As shown in the electrophoresis photograph of FIG. 2, the presence of lactoferrin and lysozyme C was confirmed in the human rhinal mucosa. The presence of lactoferrin and lysozyme C in the human rhinal mucosa was checked as follows.

A rhinal mucosa sample (upper pharyngeal mucosa) was collected from a healthy subject with a swab ("men-tip" produced by JCB Industry Limited) and was suspended in 300 μL of phosphate-buffered saline (PBS) per swab. The obtained suspension was subjected to a gel filtration chromatography (mobile phase: phosphate-buffered saline, column HiLoad 16/60 Superdex200 pg, produced by GE Healthcare) and size-fractionated into four fractions (F1 to F4). Further, the suspension was subjected to the ProteinG affinity spin column (produced by Dojindo Laboratories) and a column-bound fraction was obtained. The gel filtration fractional preparation and affinity column-bound fraction were subjected to the SDS polyacrylamide gel electrophoresis (SDS-PAGE) using the SuperSep Ace 10-20% linear gradient acrylic amide gel (produced by Wako Pure Chemical Industries, Ltd.), and a protein band was detected by performing silver staining with the Silver MS Stain (produced by Wako Pure Chemical Industries, Ltd.). With respect to the bands enclosed in boxes in FIG. 2, proteins were extracted using the Easy Separator (produced by Wako Pure Chemical Industries, Ltd.) and subjected to the liquid chromatography/tandem mass spectrometry (produced by SYNAPT LC/MS/MS, Waters). Using the MASCOT program based on the obtained data, proteins estimated from the molecular weights of the peptide fragments obtained by the mass spectrometry were searched. As a result, the band of about 80 kDa shown in FIG. 2 was identified as human-derived lactoferrin and the band of 14 kDa shown in FIG. 2 was identified as human-derived lysozyme C.

Example 2

Figure 3:
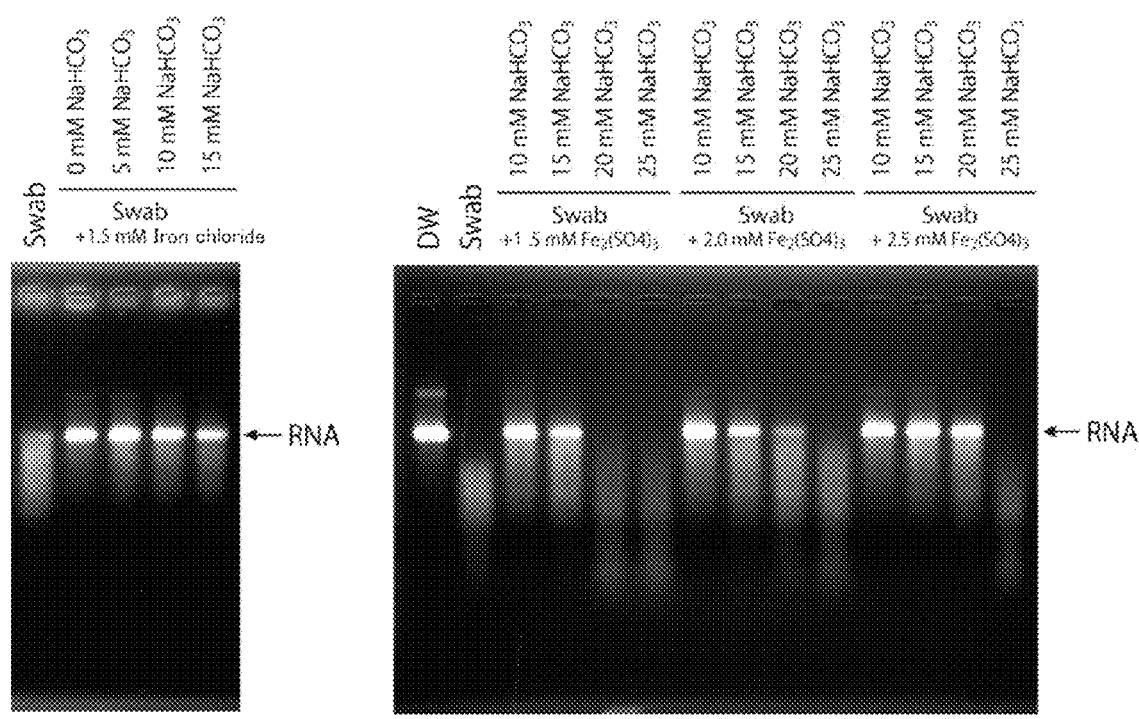
FIG. 3 is an electrophoresis photograph showing an inhibitory effect of iron ion and carbonate ion on RNA degradation activity due to lactoferrin.

Inhibitory Effect of Iron Ion and Carbonate Ion on RNA Degradation Activity Due to Human Lactoferrin As shown in FIG. 3, the inhibitory effect of iron ion and carbonate ion on the RNA degradation activity due to human lactoferrin was checked.

In Example 2, the same synthesized template RNA was used as a substrate to the RNA degradation activity (RNase activity). With respect to the left view on FIG. 3, a rhinal mucosa sample (upper pharyngeal mucosa) was collected from a healthy subject with a swab ("men-tip", produced by JCB Industry Limited) and suspended in 250 μL of 40 mM Tris-HCl (pH 7.5). Next, 1.5 mM iron chloride was added to 9 μL of the suspension, further, 5, 10, or 15 mM $NaHCO_3$ was added thereto, and the resultant was adjusted such that the final capacity becomes 18 μL. Thereafter, the suspension was incubated at 37° C. for 10 minutes. 10 μL of 50 ng/μL RNA was added to 2.5 μL of the suspension and incubated at 25° C. for 10 minutes. After the reaction, the reaction solution was subjected to 3.0% NuSieveGTG agarose gel electrophoresis (at 100V for 30 minutes), and an RNA band was detected by the ethidium bromide (EtBr) staining method.

With respect to the right view on FIG. 3, a rhinal mucosa sample of a healthy subject was suspended in 250 μL of 40 mM MES (pH 5.8), then 1.5, 2.0, or 2.5 mM $Fe_2(SO_4)_3$ and 10, 15, 20, or 25 mM $NaHCO_3$ were added to 9 μL of the suspension, and the resultant was adjusted such that the final capacity becomes 18 μL. After that, the same operations as described above were performed and an RNA band was detected by the agarose electrophoresis.

Example 3

Heat Treatment Effect on Iron Ion and Carbonate Ion

Figure 4:
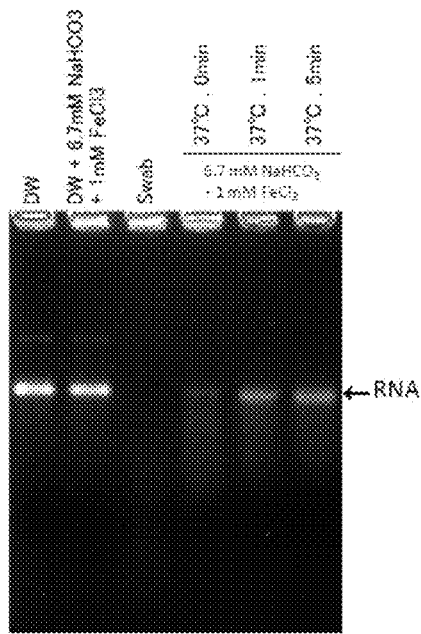
FIG. 4 is an electrophoresis photograph showing an example of an effect of heat treatment on iron ion and carbonate ion.

As shown in FIG. 4, by applying heat treatment, the RNA degradation activity inhibitory action of iron ion and carbonate ion could be increased in a short amount of time.

In Example 3, a rhinal mucosa sample of a healthy subject was suspended in 250 μL of 20 mM MES (pH 5.8) and 10% (w/v) Tween 20, 1 mM $Fe_2(SO_4)_3$ and 6.7 mM $NaHCO_3$ were added to 10 μL of the suspension, and the resultant was adjusted such that the final capacity becomes 18 μL. Thereafter, the incubation was performed at 37° C. for 0, 1 or 5 minutes. After the reaction, the reaction solution was subjected to 3.0% NuSieveGTG agarose gel electrophoresis (at 100 V for 30 minutes), and the RNA degradation activity was checked by detecting an RNA band by the ethidium bromide (EtBr) staining method.

Example 4

Figure 5:
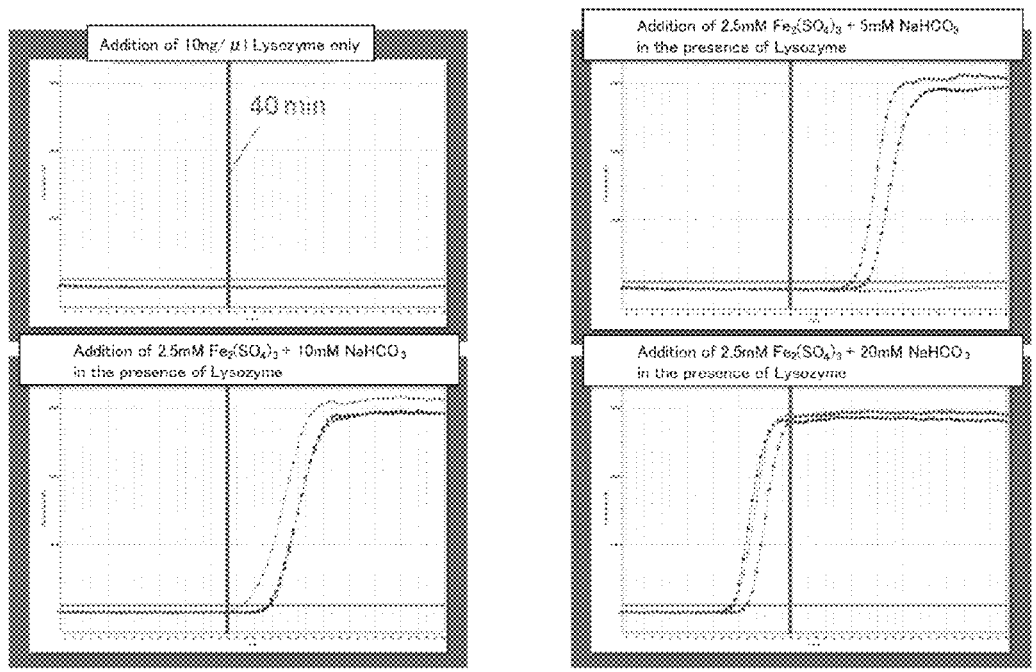
FIG. 5 shows graphs showing an example of the inhibition of reverse transcription inhibitory activity due to lysozyme C by iron ion and carbonate ion.

Inhibition of Reverse Transcription Inhibitory Activity Due to Lysozyme C by Iron Ion and Carbonate Ion As shown in FIG. 5, the reverse transcription inhibitory activity due to human lysozyme C could be inhibited by iron ion and carbonate ion.

In Example 4, the same RT-SmartAmp method as described was used. Each nucleic acid amplification activity in the case where, in 25 μL of the reaction solution of the RT-SmartAmp method, human-derived purified lysozyme C (produced by CALNIOCHEM) was added at the final concentration of 10 ng/mL and 0 or 2.5 mM $Fe_2(SO_4)_3$ and 0, 5, 10, or 20 mM $NaHCO_3$ were added to the reaction solution was compared by a fluorescence amplification curve.

Example 5

Synergistic Effect Between Iron Ion and Carbonate Ion and SDS

Figure 6:
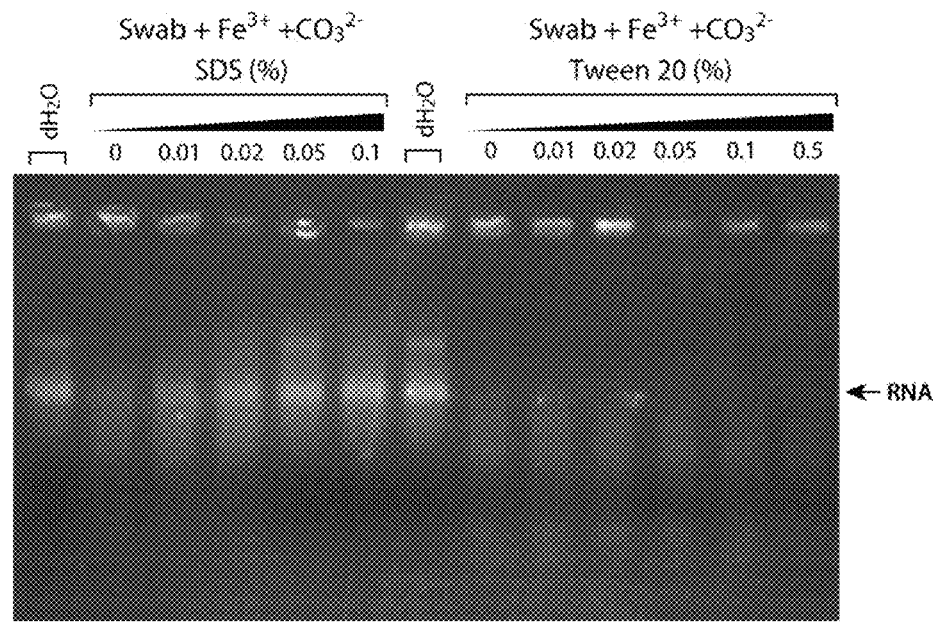
FIG. 6 is an electrophoresis photograph showing an example of a synergistic effect between iron ion and carbonate ion, and SDS.

As shown in FIG. 6, the RNA degradation activity could be improved in the presence of iron ion and carbonate ion at a low concentration.

In Example 5, a rhinal mucosa sample of a healthy subject was suspended in 250 μL of 40 mM MES (pH 5.8), then 2.5 mM $Fe_2(SO_4)_3$ and 20 mM $NaHCO_3$ were added to 9 μL of the suspension, further, SDS (final concentration: 0, 0.01, 0.02, 0.05, or 0.1%) as a polar surfactant or Tween 20 (final concentration: 0, 0.01, 0.02, 0.05, 0.1, or 0.5%) as a nonionic surfactant was added, and the resultant was adjusted such that the final capacity becomes 18 μL. Thereafter, the incubation was performed at 37° C. for 10 minutes. To 2.5 μL of the suspension, 10 μL of 50 ng/μL RNA was added and the incubation was performed at 25° C. for 10 minutes. After the reaction, the reaction solution was subjected to 3.0% NuSieveGTG agarose gel electrophoresis (at 100V for 30 minutes), and an RNA band was detected by the ethidium bromide (EtBr) staining method.

Reference Example 2

Influence of Removal of SDS from Pretreatment Reagent by Addition of Alumina

Figure 8:
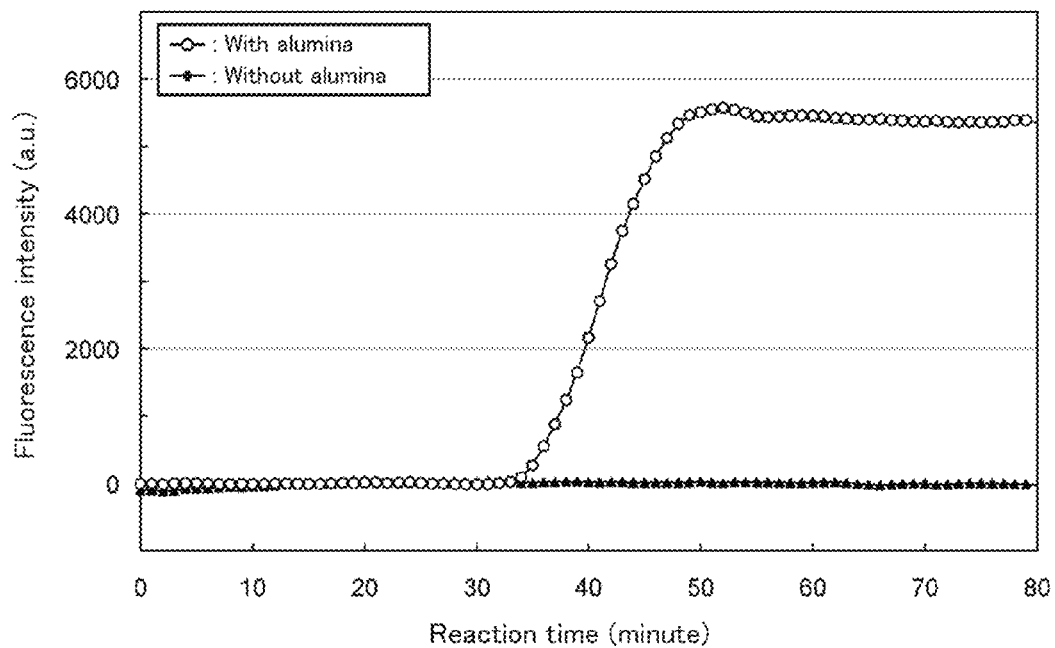
FIG. 8 is a graph showing an example of an influence of SDS removal by addition of alumina.

As shown in FIG. 8, by adding alumina to the pretreatment reagent, SDS contained in the pretreatment reagent of the present invention could be removed, and this resulted in achieving the nucleic acid amplification of the template RNA. Reference Example 2 was performed under the condition not containing the human rhinal mucosa for checking only the activity of SDS on the nucleic acid amplification suppression.

In the RT-SmartAmp method in Reference Example 2, the sequence of influenza A(H3N2), the NA region 675-1075 bases, was used as a template RNA to be amplified. For preparing the template RNA, first, PCR was performed using cDNA having the sequence complementary to the NA region, the following primer 3 (SEQ ID NO: 9) and primer 4 (SEQ ID NO: 10), and Prime STAR (produced by TAKARA BIO INC.) as an enzyme for PCR.

```
Primer 3
                                       (SEQ ID NO: 9)
5'-TAATACGACTCACTATAGGGCCAGGAGTCAGAATGCGTTT-3'

Primer 4
                                      (SEQ ID NO: 10)
5'-GCCTTTCACTCCATGACCAC-3'
```

Conditions for the PCR were as follows. That is, one cycle of treatment at 98° C. for 10 seconds, 55° C. for 5 seconds, 72° C. for 30 seconds was repeated for 30 cycles, and then incubation at 72° C. for 4 minutes was performed. With the DNA fragment amplified by this PCR, the template RNA was synthesized using the CUGA7 in-vitro Transcription Kit (produced by NIPPON GENE CO., LTD.).

In the RT-SmartAmp method, the primers (SEQ ID NOs: 11 to 15, produced by Kabushiki Kaisha DNAFORM) and exciton primer (SEQ ID NO: 16, produced by Kabushiki Kaisha DNAFORM, see Japanese Patent No. 4370385) having the following sequences and concentrations and the synthesized template RNA were added to a solution that contains 1.4 mM dNTP, 5% DMSO, 20 mM Tris-HCl (pH 8.0), 30 mM potassium acetate, 10 mM sodium sulfate, 8 mM magnesium sulfate, 0.1% Tween 20, 12 unit Aac DNA polymerase, and 0.125 unit AMV Reverse Transcriptase (these concentrations are the final concentrations), and the resultant was used as a reaction solution.

```
FP primer 1
     (SEQ ID NO: 11, final concentration: 1.82 µM)
5'-TTTATATATATATAAACATGTCGAGGAGTG-3'

TP primer 1
     (SEQ ID NO: 12, final concentration: 1.82 µM)
5'-CCTCGATATCCTGGTATGGGCCTATTGGA-3'

OP primer 3
     (SEQ ID NO: 13, final concentration: 0.23 µM)
5'-GCACATTGTCAGGAAGTGC-3'

OP primer 4
     (SEQ ID NO: 14, final concentration: 0.23 µM)
5'-TTTTTCTGGGTGTGTCTCC-3'

BP primer 1
     (SEQ ID NO: 15, final concentration: 0.68 µM)
5'-TGTGTCTGCAGAG-3'

BP exciton primer1
     (SEQ ID NO: 16, final concentration: 0.23 µM)
5'-TGTGZCTGCAGAG-3'
(Z indicates thymine residue labeled with exciton)
```

As the pretreatment reagent, a solution was prepared by adding 0.1% SDS to a solution that contains 20 mM MES buffer (pH 5.8), 2.5 mM iron sulfate, and 20 mM sodium hydrogen carbonate. The activated alumina (produced by Wako Pure Chemical Industries, Ltd., molecular weight: 101.96) was added to this pretreatment reagent at the final concentration of 1 mg/ml, and suspended by stirring using a vortex mixer. Thereafter, the suspension was placed on an empty column, Micro Bio-Spin Chromatography Column (produced by BIO-RAD), having a sintered glass filter, and a filtrate from which alumina to which SDS is adsorbed was removed was obtained by centrifugation at 1200×g for 1 minute. Further, as a comparative example, the same treatment as described above was performed without adding alumina to obtain a filtrate. The remaining activity of SDS (DNA polymerase inhibitory activity) was compared by checking the presence or absence of the nucleic acid amplification activity with respect to the obtained filtrate using the reaction solution of the RT-SmartAmp method.

5 µL of the filtrate treated in the manner described above was added to the reaction solution of the RT-SmartAmp, the resultant was adjusted such that the final capacity of the solution becomes 25 µL per reaction, then the reaction under a constant temperature was performed using the real-time PCR apparatus MX3000p (produced by Agilent Technologies, Inc.) at 60° C. for 90 minutes, and the nucleic acid amplification activity was checked by obtaining a fluorescence amplification curve via an FAM filter. The presence of residual of SDS that causes the nucleic acid amplification inhibition was evaluated based on whether or not rising in the amplification curve was seen. As shown in FIG. 8, it was recognized that prominent nucleic acid amplification was achieved only when alumina was added. Therefore, it was determined that it is possible to remove SDS from the pretreatment reagent of the present invention by adding alumina.

Reference Example 3

Influence of Removal of SDS from Pretreatment Reagent by Ultrafiltration Filter

Figure 9:
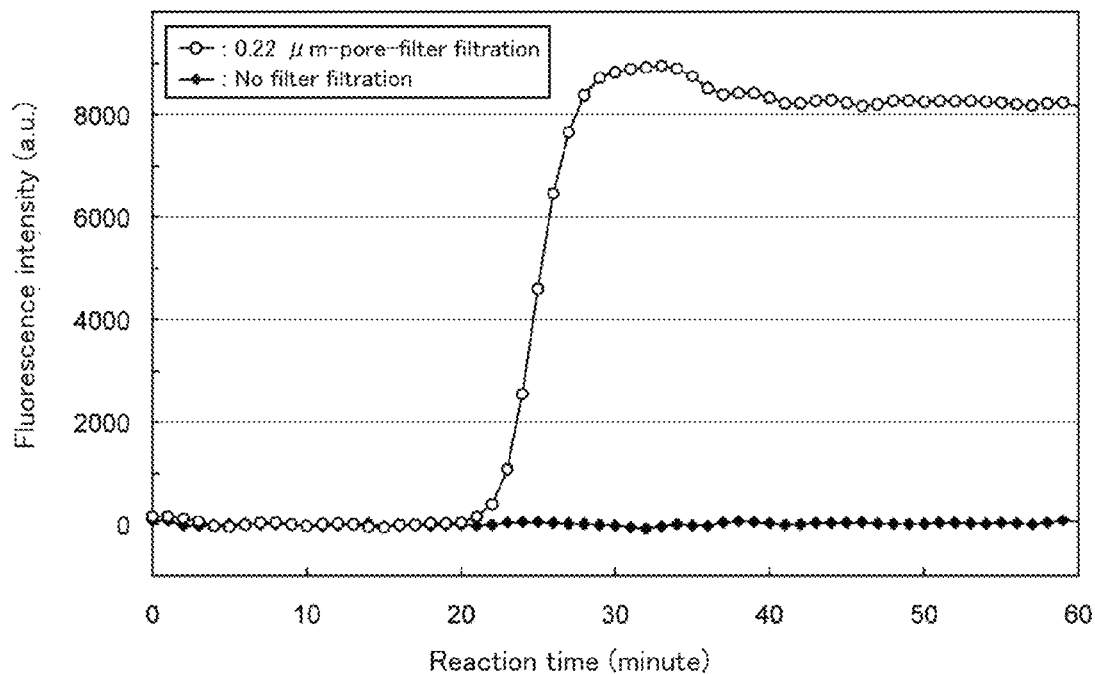
FIG. 9 is a graph showing an example of an influence of SDS removal by increase in iron ion concentration and an ultrafiltration filter.

As shown in FIG. 9, by increasing the concentration of iron ion contained in the pretreatment reagent of the present invention, formation of a precipitate of SDS was promoted. By applying treatment of passing (filtrating) the precipitate through the ultrafiltration filter, SDS contained in the pretreatment reagent could be removed, and the nucleic acid amplification of the template RNA could be achieved. Reference Example 3 was performed under the condition not containing the human rhinal mucosa for checking only the activity of SDS on the nucleic acid amplification suppression.

As the pretreatment reagent, a solution was prepared by adding 0.1% SDS to a solution that contains 20 mM MES buffer (pH 5.8), 5 mM iron sulfate, and 20 mM sodium hydrogen carbonate. The concentration of iron ion in this pretreatment reagent is set higher than that of the pretreatment reagent in Example 1. This pretreatment reagent was allowed to be passed through the Millex HV (φ13 mm, membrane pore size: 0.22 µm, produced by Millipore Corporation) using a syringe to obtain a filtrate. The remaining activity of SDS (DNA polymerase inhibitory activity) was compared with the case in which the pretreatment reagent was used without filter filtration by checking the presence or absence of the nucleic acid amplification activity with respect to the obtained filtrate using the reaction solution of the RT-SmartAmp method described in Reference Example 2.

5 µL of the filtrate treated in the manner described above was added to the reaction solution of the RT-SmartAmp, the resultant was adjusted such that the final capacity of the solution becomes 25 µL per reaction, then the reaction under a constant temperature was performed using the real-time PCR apparatus MX3000p (produced by Agilent Technologies, Inc.) at 60° C. for 90 minutes, and the nucleic acid amplification activity was checked by obtaining a fluorescence amplification curve via an FAM filter. The residuality of SDS that causes the nucleic acid amplification inhibition was evaluated based on whether or not rising in the amplification curve was seen. As shown in FIG. 9, nucleic acid amplification was not recognized in the case where the filter filtration was not performed but it was recognized that prominent nucleic acid amplification was achieved in the case where the filtration was performed with an ultrafiltration filter having the membrane pore size of 0.22 μm. Therefore, it was determined that it is possible to remove SDS from the pretreatment reagent of the present invention by removing the precipitate of SDS formed in accordance with the increase in the concentration of iron ion in the pretreatment reagent by ultrafiltration filter treatment.

Reference Example 4

Figure 10:
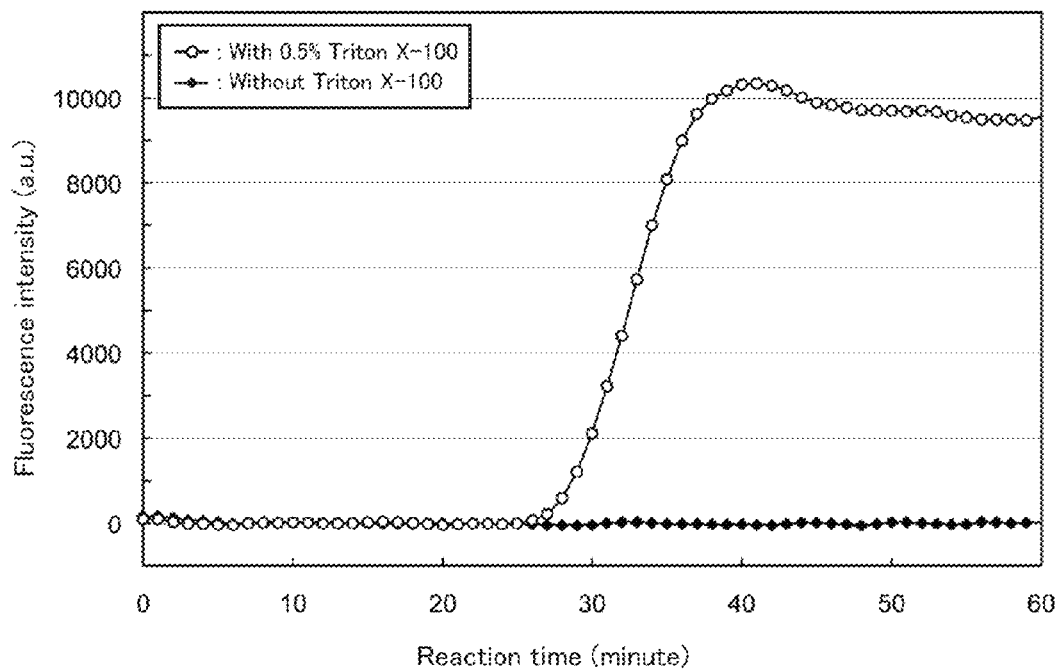
FIG. 10 is a graph showing an example of the mitigation effect of Triton X-100 on a nucleic acid amplification inhibition due to SDS in a nucleic acid amplification reaction.

Mitigation Effect of Triton X-100 on Nucleic Acid Amplification Inhibition Due to SDS in Nucleic Acid Amplification Reaction As shown in FIG. 10, in the case where SDS was added directly to a nucleic acid amplification reaction solution, by preliminarily adding the Triton (registered trademark) X-100, which is a nonionic surfactant, to the nucleic acid amplification reaction solution, the nucleic acid amplification inhibition of SDS contained in the pretreatment reagent could be mitigated. Reference Example 4 was performed by adding SDS alone to the RT-SmartAmp for checking only the activity of SDS on the nucleic acid amplification suppression.

The Triton X-100 was added to the reaction solution of the RT-SmartAmp method described in Reference Example 2 such that the final concentration thereof becomes 0% or 0.5%, and 5 μL of 0.1% SDS solution was added thereto such that the final capacity becomes 25 μL per reaction.

With respect to the reaction solution, the reaction under a constant temperature was performed using the real-time PCR apparatus MX3000p (produced by Agilent Technologies, Inc.) at 60° C. for 90 minutes, and the nucleic acid amplification activity was checked by obtaining a fluorescence amplification curve via an FAM filter. The inhibitory effect of SDS on nucleic acid amplification was evaluated based on whether or not rising in the amplification curve was seen. As shown in FIG. 10, prominent nucleic acid amplification was recognized in the case where 0.5% Triton X-100 was added to the reaction solution. Therefore, it was determined that it is possible to mitigate the nucleic acid amplification inhibition due to SDS by the Triton X-100 and to achieve the nucleic acid amplification from the template RNA even in the case where SDS was present in the nucleic acid amplification reaction solution.

Example 6

Detection of RNA Virus Contained in Human Rhinal Mucosa

Figure 11:
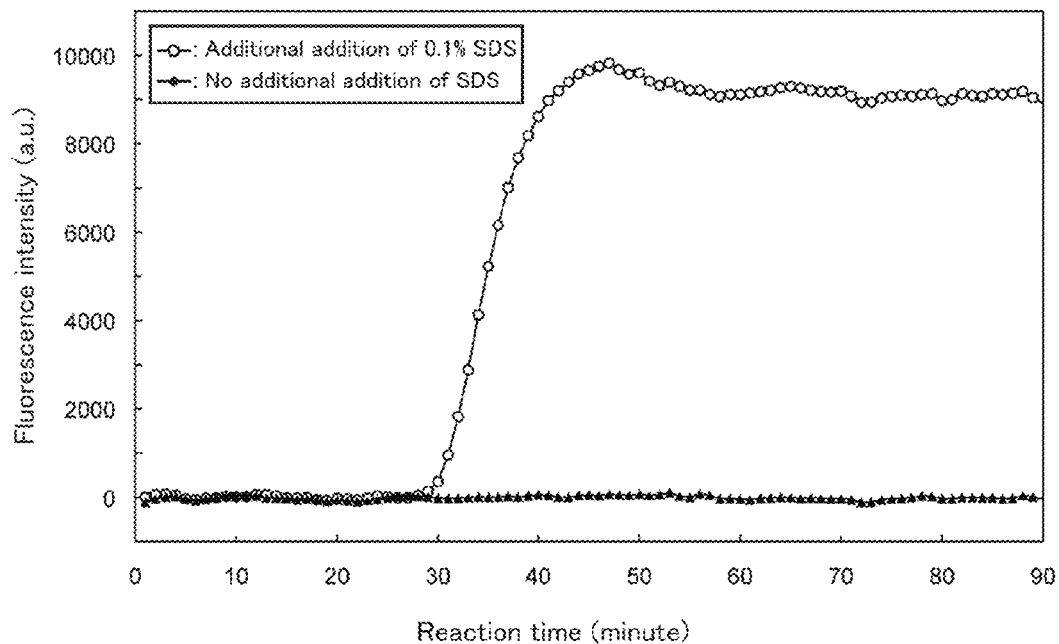
FIG. 11 is a graph showing that RNA virus contained in the human rhinal mucosa could be detected by the RT-SmartAmp method.

By performing the steps described in the Reference Examples 2 to 4 under the condition in which SDS was added to the pretreatment reagent of the present invention that contains iron ion and carbonate ion, as shown in FIG. 11, RNA virus contained in the human rhinal mucosa could be detected by the RT-SmartAmp method.

As the pretreatment reagent, a solution was prepared by adding 0.1% SDS to a solution that contains 20 mM MES buffer (pH 5.8), 5 mM iron sulfate, and 20 mM sodium hydrogen carbonate. The human rhinal mucosa and influenza A(H3N2) of $10^4$ pfu/mL were suspended in 500 μL of the aforementioned pretreatment reagent. After suspension, 0.1% SDS was added to the suspension for breaking down the virus outer membrane. Thereafter, the resultant was allowed to be passed through the Millex HV (φ13 mm, membrane pore size: 0.22 μm, produced by Millipore Corporation) using a syringe, and the filtrate thus obtained was used as a pretreated sample. Further, a comparative example used a sample obtained by filter-filtrating the pretreatment reagent to which 0.1% SDS for breaking down the virus outer membrane was not added.

In the RT-SmartAmp method, to a solution that contains 1.4 mM dNTP, 5% DMSO, 20 mM Tris-HCl (pH 8.0), 30 mM potassium acetate, 10 mM sodium sulfate, 8 mM magnesium sulfate, 0.1% Tween 20, 12 unit Aac DNA polymerase, and 0.125 unit AMV Reverse Transcriptase (these concentrations are the final concentrations), the Triton X-100 was added such that the final concentration becomes 0.5% and the primers (SEQ ID NOs: 11 to 15, produced by Kabushiki Kaisha DNAFORM) and exciton primer (SEQ ID NO: 16, produced by Kabushiki Kaisha DNAFORM, see Japanese Patent No. 4370385) having the sequences and concentrations described in Reference Example 2 were added, and the resultant was used as a reaction solution.

5 μL of the aforementioned pretreated sample was added to the reaction solution, the resultant was adjusted such that the final capacity of the solution becomes 25 μL per reaction, then the reaction under a constant temperature was performed using the real-time PCR apparatus MX3000p (produced by Agilent Technologies, Inc.) at 60° C. for 90 minutes, and the nucleic acid amplification activity was checked by obtaining a fluorescence amplification curve via an FAM filter. As shown in FIG. 11, the nucleic acid amplification was achieved and the nucleic acid amplification from the RNA virus could be detected only with respect to the pretreated reagent to which 0.1% SDS was further added for breaking down the virus outer membrane.

The invention claimed is:

1. A method of detecting RNA in a sample collected from a living body, the sample containing lactoferrin, the method comprising:
   applying an inhibition treatment of RNA degradation activity due to lactoferrin to the sample collected from the living body;
   applying an inhibition treatment of reverse transcription inhibitory activity due to lysozyme C to the sample collected from the living body; and
   an RNA detection step of detecting RNA in the treated sample,
   wherein the inhibition treatment of RNA degradation activity due to lactoferrin is applied to the sample collected from the living body by adding an inhibitor of RNA degradation activity due to lactoferrin to the sample collected from the living body,
   wherein the inhibitor is at least one selected from the group consisting of copper, nickel, iron, gold, scandium, yttrium, gadolinium, cerium, neodymium, and zinc,
   wherein the inhibition treatment of reverse transcription inhibitory activity due to lysozyme C is applied to the sample collected from the living body by adding an inhibitor of reverse transcription inhibitory activity due to lysozyme C to the sample collected from the living body, and
   wherein at least one of the RNA degradation activity inhibitor and the inhibitor of reverse transcription inhibitory activity contains an iron ion agent and a carbonate ion agent.

2. The method according to claim 1, wherein in the RNA detection step, a surfactant is added to the treated sample.

3. The method according to claim 2, wherein the surfactant is a nonpolar surfactant.

4. The method according to claim 1, wherein the sample collected from the living body includes at least one selected from the group consisting of rhinal mucosae, sinus mucosae, tracheal mucosae, saliva, secretions from the mouth or the throat, tears, milk, bile, blood (leukocyte), cervical mucosae, internal and external genitalia mucosae, amniotic fluids, and urine of a subject.

5. The method according to claim 4, wherein the subject is human.

6. The method according to claim 1, wherein the sample collected from the living body contains a human rhinal mucosa.

7. The method according to claim 1, wherein the sample collected from the living body to which the iron ion agent and the carbonate ion agent are added is applied with heat treatment.

8. The method according to claim 1, wherein a polar surfactant is added to the sample collected from the living body.

9. The method according to claim 8, wherein the polar surfactant is SDS.

* * * * *

UNITED STATES PATENT AND TRADEMARK OFFICE
CERTIFICATE OF CORRECTION

PATENT NO. : 9,518,901 B2
APPLICATION NO. : 13/807605
DATED : December 13, 2016
INVENTOR(S) : Hayashizaki et al.

It is certified that error appears in the above-identified patent and that said Letters Patent is hereby corrected as shown below:

On the Title Page

Item (56), Column 2, under "FOREIGN PATENT DOCUMENTS", Line 5, delete "DE" and insert --EP--.

Item (56), Column 2, under "OTHER PUBLICATIONS", Line 8, delete "Is" and insert --is--.

Signed and Sealed this
Eighteenth Day of April, 2017

Michelle K. Lee
*Director of the United States Patent and Trademark Office*

SEQUENCE LISTING

<160> NUMBER OF SEQ ID NOS: 16

<210> SEQ ID NO 1
<211> LENGTH: 41
<212> TYPE: DNA
<213> ORGANISM: Artificial
<220> FEATURE:
<223> OTHER INFORMATION: primer

<400> SEQUENCE: 1
ctaatacgac tcactatagg gccatctact agtgctgacc a         41

<210> SEQ ID NO 2

```
<211> LENGTH: 20
<212> TYPE: DNA
<213> ORGANISM: Artificial
<220> FEATURE:
<223> OTHER INFORMATION: primer

<400> SEQUENCE: 2
cccttcaatg aaaccggcaa                                              20

<210> SEQ ID NO 3
<211> LENGTH: 28
<212> TYPE: DNA
<213> ORGANISM: Artificial
<220> FEATURE:
<223> OTHER INFORMATION: primer

<400> SEQUENCE: 3
gcattcgcga aatgataata ccagatcc                                     28

<210> SEQ ID NO 4
<211> LENGTH: 29
<212> TYPE: DNA
<213> ORGANISM: Artificial
<220> FEATURE:
<223> OTHER INFORMATION: primer

<400> SEQUENCE: 4
ttccattgcg aatgcacatt cgaagcaac                                    29

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
acactagtag agccgggaga                                              20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
ctggtgttta tagcaccctt                                              20

<210> SEQ ID NO 7
<211> LENGTH: 16
<212> TYPE: DNA
<213> ORGANISM: Artificial
<220> FEATURE:
<223> OTHER INFORMATION: primer

<400> SEQUENCE: 7
accactagat ttccag                                                  16

<210> SEQ ID NO 8
<211> LENGTH: 16
<212> TYPE: DNA
<213> ORGANISM: Artificial
<220> FEATURE:
<223> OTHER INFORMATION: primer
<220> FEATURE:
<221> NAME/KEY: misc_feature
```

```
<222> LOCATION: (6)..(6)
<223> OTHER INFORMATION: n is an exciton labeling portion that is a
      single nucleotide

<400> SEQUENCE: 8
accacnagat ttccag                                                      16

<210> SEQ ID NO 9
<211> LENGTH: 40
<212> TYPE: DNA
<213> ORGANISM: Artificial Sequence
<220> FEATURE:
<223> OTHER INFORMATION: primer

<400> SEQUENCE: 9
taatacgact cactataggg ccaggagtca gaatgcgttt                             40

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gcctttcact ccatgaccac                                                  20

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
tttatatata tataaacatg tcgaggagtg                                       30

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
cctcgatatc ctggtatggg cctattgga                                        29

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
gcacattgtc aggaagtgc                                                   19

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
tttttctggg tgtgtctcc                                                   19
```

```
<210> SEQ ID NO 15
<211> LENGTH: 13
<212> TYPE: DNA
<213> ORGANISM: Artificial Sequence
<220> FEATURE:
<223> OTHER INFORMATION: primer

<400> SEQUENCE: 15
tgtgtctgca gag                                                        13

<210> SEQ ID NO 16
<211> LENGTH: 13
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (5)..(5)
<223> OTHER INFORMATION: n is an exciton labeling portion that is a
      single nucleotide

<400> SEQUENCE: 16
tgtgnctgca gag                                                        13
```